US009097639B2

(12) United States Patent
Potyrailo et al.

(10) Patent No.: US 9,097,639 B2
(45) Date of Patent: Aug. 4, 2015

(54) SYSTEMS FOR ANALYSIS OF FLUIDS

(71) Applicant: General Electric Company, Schenectady, NY (US)

(72) Inventors: Radislav Alexandrovich Potyrailo, Niskayuna, NY (US); Yongjae Lee, Niskayuna, NY (US); Victoria Eugenia Cotero, Niskayuna, NY (US); Jon Albert Dieringer, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 294 days.

(21) Appl. No.: 13/729,800

(22) Filed: Dec. 28, 2012

(65) Prior Publication Data

US 2014/0182362 A1    Jul. 3, 2014

(51) Int. Cl.
*G01N 27/02* (2006.01)
(52) U.S. Cl.
CPC .................................. *G01N 27/026* (2013.01)
(58) Field of Classification Search
CPC ................................................... G01N 27/026
USPC .............................. 73/64.53, 579; 340/572.1
See application file for complete search history.

(56) References Cited

U.S. PATENT DOCUMENTS

| | | | | |
|---|---|---|---|---|
| 5,025,346 A * | 6/1991 | Tang et al. | ................. | 361/283.1 |
| 5,592,040 A * | 1/1997 | Yamamoto | ................ | 310/313 D |
| 7,456,744 B2 | 11/2008 | Kuhns et al. | | |
| 7,911,345 B2 | 3/2011 | Potyrailo et al. | | |
| 7,948,385 B2 | 5/2011 | Potyrailo et al. | | |
| 8,246,910 B2 | 8/2012 | Dhirani et al. | | |
| 2002/0050929 A1* | 5/2002 | Parrotta et al. | ............. | 340/572.1 |
| 2002/0154029 A1 | 10/2002 | Watters et al. | | |
| 2007/0090926 A1 | 4/2007 | Potyrailo et al. | | |
| 2007/0090927 A1 | 4/2007 | Potyrailo et al. | | |
| 2008/0135614 A1 | 6/2008 | Werner et al. | | |
| 2009/0278685 A1 | 11/2009 | Potyrailo et al. | | |
| 2011/0101996 A1 | 5/2011 | Potyrailo et al. | | |
| 2012/0116683 A1 | 5/2012 | Potyrailo et al. | | |
| 2012/0161787 A1 | 6/2012 | Potyrailo et al. | | |
| 2012/0235690 A1 | 9/2012 | Potyrailo et al. | | |

FOREIGN PATENT DOCUMENTS

GB    2486786 A    6/2012

OTHER PUBLICATIONS

Potyrailo et al., "Passive Multivariable Temperature and Conductivity RFID Sensors for Single-Use Biopharmaceutical Manufacturing Components", Biotechnology Progress, pp. 875-884, vol. 27, Issue 3, May 2011.

Amrani et al., "Multi-Frequency Interrogation Technique Applied to Conducting Polymer Gas and Odour Sensors", IEE Proceedings Science, Measurement & Technology, pp. 95-101, vol. 146, 1999.

(Continued)

*Primary Examiner* — J M Saint Surin
(74) *Attorney, Agent, or Firm* — Eileen B. Gallagher

(57)            ABSTRACT

A resonant sensor assembly includes a dielectric substrate having a sensing region. The sensor assembly further comprises a plurality of tuning elements operatively coupled to the sensing region, where the sensing region is coupled to the plurality of tuning elements to define a plurality of resonant circuits.

22 Claims, 6 Drawing Sheets

(56) References Cited

OTHER PUBLICATIONS

Gawad et al., "Micromachined Impedance Spectroscopy Flow Cytometer for cell Analysis and Particle Sizing", Lab on a Chip, pp. 76-82, vol. 1, 2001.
Cheung et al., "Impedance Spectroscopy Flow Cytometry: on-Chip Label-Free cell Differentiation", Cytometry Part A, pp. 124-132, vol. 65, 2005.
Potyrailo et al., "Multianalyte Chemical Identification and Quantitation Using a Single Radio Frequency Identification Sensor", Analytical Chemistry, pp. 45-51, vol. 79, No. 1, Jan. 2007.
Potyrailo et al., "Position-Independent Chemical Quantitation with Passive 13.56-Mhz Radio Frequency Identification (RFID) Sensors", Talanta, pp. 624-628, vol. 75, 2008.
Zheng et al., "Resonance Impedance Sensing of Human Blood Cells", Sensors and Actuators A: Physical, pp. 29-36, vol. 145-146, 2008.
Potyrailo et al. "RFID Sensors as the Common Sensing Platform for Single-Use Biopharmaceutical Manufacturing", Measurement Science and Technology, vol. 22, Issue 8, 2011.
Search Report and Written Opinion from PCT Application No. PCT/SE2013/051589 dated May 6, 2014.
Search Report and Written Opinion from PCT Application No. PCT/SE2013/051590 dated May 6, 2014.
Potyrailo et al. "Integration of Passive Multivariable RFID Sensors into Single-Use Biopharmaceutical Manufacturing Components", RFID, 2010 IEEE International Conference, Apr. 2010, pp. 1-7.
Ehret et al., "On-line control of Cellular Adhesion with Impedance Measurements Using Interdigitated Electrode Structures", Medical & Biological Engineering & Computing, pp. 365-370, vol. 36, 1998.
Ertl et al., "Interdigitated Impedance Sensors for Analysis of Biological Cells in Microfluidic Biochips", E & I Elektrotechnik und Informationstechnik, pp. 47-50, vol. 126, Issue 1-2, Feb. 2009.
Alexander et al., "Optimization of Interdigitated Electrode (IDE) Arrays for Impedance Based Evaluation of Hs 578T Cancer Cells", Journal of Physics: Conference Series, pp. 1-4, vol. 24, Issue 1, 2010.
Bianchi et al., "Model of an Interdigitated Microsensor to Detect and Quantify Cells Flowing in a Test Chamber", 6th annual COMSOL Conference Paris, pp. 1-5, Nov. 2010.

\* cited by examiner

SYSTEMS FOR ANALYSIS OF FLUIDS

BACKGROUND

The invention relates generally to systems and methods for analysis of fluids, and more particularly to systems and methods for analysis of fluids using resonant sensors.

Typically, resonant sensors are used to provide information about physical, chemical, and biological constituents present in a sample. Selectivity of sensors is desirable in sensor performance and applications. Typically, lack of selectivity prevents the wide use of sensors in sensing physical, chemical, and biological species in fluids in applications such as but not limited to, medical diagnostics, life sciences, water, oil and gas, and security. Impedance spectroscopy is often used for materials science and materials characterization. Impedance spectroscopy provides a number of advantages in the analysis of biological species as it provides a non-invasive, non-toxic platform for analysis of biological species. However, the well-accepted limitations of traditional impedance spectroscopy include relatively low sensitivity and prohibitively long acquisition times over the broad frequency range.

Current laboratory techniques often utilize a plurality of pre-treatment steps for the sample and require a pathologist or a technician to manually identify the sample composition. Current sensor techniques utilize different transducers based on optical, electrical, mechanical, thermal, and magnetic detection principles. The sensors may be resonant or non-resonant. The resonant transducers provide a mechanism to more accurately probe the dielectric properties of any samples in the presence of uncontrolled ambient environmental noise contributions as compared to non-resonant transducers. Non-limiting examples of ambient environmental noise contributions include temperature, media composition, and presence of interferences in the sample.

BRIEF DESCRIPTION

In one embodiment, a resonant sensor assembly includes a dielectric substrate having a sensing region. The sensor assembly further comprises a plurality of tuning elements operatively coupled to the sensing region, wherein the sensing region is coupled to the plurality of tuning elements to define a plurality of resonant circuits.

In another embodiment, a system includes a resonant sensor assembly and a reader in operative communication with the resonant sensor, where the reader is configured to acquire responses at a plurality of frequencies. The resonant sensor assembly includes a dielectric substrate comprising a sensing region, and a plurality of tuning elements operatively coupled to the sensing region. The sensing region is coupled to the plurality of tuning elements to define a plurality of resonant circuits.

In yet another embodiment, the resonant sensor assembly includes a dielectric substrate comprising a sensing region with at least four inter-digital electrode structure, and a plurality of tuning elements operatively coupled to the sensing region. The sensing region is coupled to the plurality of tuning elements configured to provide predetermined resonant frequencies associated with the plurality of electrode pairs to define a plurality of resonant circuits.

DRAWINGS

These and other features, aspects, and advantages of the invention will become better understood when the following detailed description is read with reference to the accompanying drawings in which like characters represent like parts throughout the drawings, wherein.

DETAILED DESCRIPTION

Figure 1:
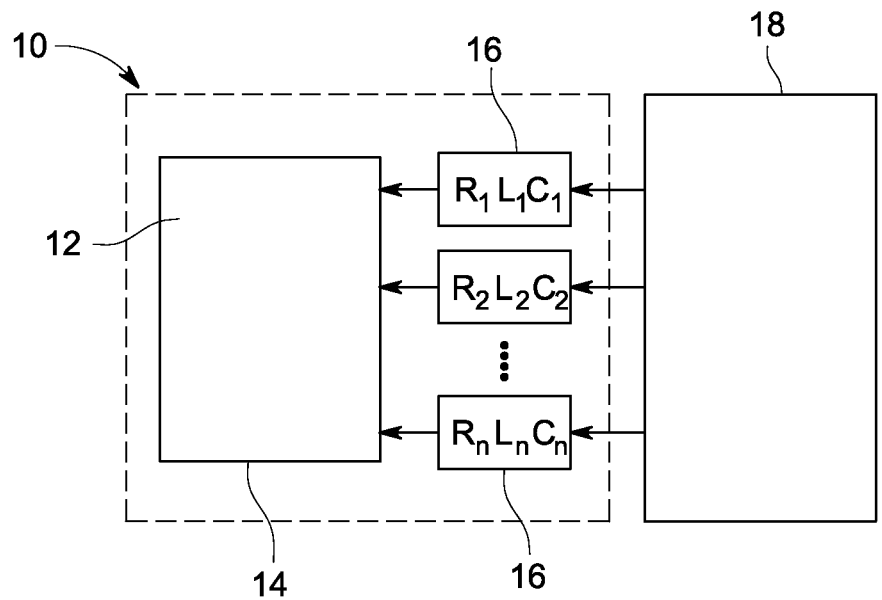
FIG. 1 is a schematic view of a portion of an example sensor system employing a sensor assembly configured to probe a fluid sample using a plurality of frequencies, in accordance with embodiments of the present technique.

Embodiments relate to systems and methods for physical, chemical and/or biological detection. In certain embodiments, the systems and methods may be used for analysis of fluids. Advantageously, the systems and methods facilitate probing the fluids at various frequencies using a single sensor. In certain embodiments, a resonant sensor assembly may comprise a single sensing region that is configured to resonate at a plurality of frequencies. In some of these embodiments, the single sensing region is configured to probe a fluid at a plurality of frequencies. Various sub-regions in the single sensing region may be configured to probe different depths in the fluid sample providing tomographic information about the fluid sample in the direction perpendicular to a sensor plane. This tomographic information may be provided through the use of electromagnetic field penetrating waves. In one example, the electromagnetic waves may include electric field penetrating waves and magnetic field penetrating waves. For example, if the fluid sample contains cells or other constituents in the sample, the tomographic information may include information about complex permittivity of the sample as a function of the distance from the sensing surface. The information obtained from different depths within the cell provides an indication of the cell adhesion, migration of new cells, changes in cell activity and response to external stimuli (e.g. environmental, pharmacologic). In one example, information on cell morphology may be used to track the metastasis of cancer cells in rapid collected biopsies.

In certain embodiments, the sensor may be employed in one or more applications in the field of medical diagnostics, life sciences, water technologies, oil and gas, and security. In the case of medical diagnostics, the resonant sensor assembly may be used to detect or diagnose an infection or cancer. In the case of water technologies, the resonant sensor assembly may be used to detect protein and bacterial cells accumulation in a water sample. The water sample may be from drinking water, or distillation or cooling tanks.

Advantageously, since the systems and methods facilitate probing a sample with a plurality of frequencies while using a single sensor, it is not required to dispose the fluid sample on a plurality of sensors to probe the sample with a plurality of frequencies.

In certain embodiments, a resonant sensor assembly may include a dielectric substrate comprising a sensing region, a plurality of tuning elements operatively coupled to the sensing region. Further, the sensing region is coupled to the plurality of tuning elements to define a plurality of resonant circuits. Each resonant circuit may be used to define a sub-region in the single sensing region, where each sub-region is configured to probe different depths in the fluid sample. In one embodiment, the dielectric substrate and the sensing region may be a part of a resonant sensor. In certain embodiments, the resonant circuits may include components that in combination result in producing resonance sensor response.

In some embodiments, the resonant sensor may be coupled to the plurality of tuning elements to define a plurality of resonant circuits. In one embodiment, the tuning elements may be external to the resonant sensor. In another embodiment, the tuning elements may not be external to the resonant sensor, the tuning elements may be integral to the resonant sensor In some embodiments, a sensor reader may be configured to monitor a plurality of responses from the resonant sensor assembly. The reader may be in operative association with the sensor through a reader antenna. In one embodiment, the reader may be configured to monitor a resonance property of the resonant sensor. The data from the resonant sensor may be transferred using a wired or a wireless transmission. In one embodiment, the wireless transmission is inductively-coupled transmission. In certain embodiments, the reader may be a response analyzer that is configured to receive signals of a plurality of frequencies.

In certain embodiments, the sensor reader may be configured to measure real and imaginary parts of the impedance spectrum of the resonant sensor having the sample. In certain embodiments, the sensor reader may be configured to measure real and imaginary parts of the impedance spectrum of the resonant sensor that is associated with the sample outside the sensor resonance. In addition, measurements of the complex impedance spectra parameters, the reader may measure other spectral parameters, related to the complex impedance spectra. Non-limiting examples of the spectral parameters include S-parameters (scattering parameters) and Y-parameters (admittance parameters). In some embodiments, the sensor reader may be configured to monitor the sensor in real-time. Further, the reader may be configured to monitor the sensor response in an intermittent or continuous fashion.

In certain embodiments, the resonant sensor may include a single sensing region, where the sensing region is configured to resonate at a plurality of frequencies. In one example, the resonant sensor may be a RFID sensor. The RFID sensor may comprise a memory chip. The memory chip may be used to store and retrieve data when required. The data may include a digital ID of the RFID sensor, or any other information of the RFID sensor. The memory chip may be a read-write chip, such as an integrated circuit (IC) chip. Alternatively, the memory chip may be a read-only chip, such as an acoustic wave device chip. The memory chip may be an analog input for a separate sensor.

As used herein the term "RFID tag" refers to a data storage and reporting technology that uses electronic tags for storing data and which contains at least two components where the first component is an integrated circuit (memory chip) for storing and processing information, and modulating and demodulating a radio frequency signal. This memory chip may also be used for other specialized functions, for example it can contain a capacitor. In one embodiment, the memory chip may also contain an input for an analog signal. The second component is an antenna for receiving and transmitting the radio frequency signal. The antenna may also be configured to serve as a sensing region. In certain embodiments, a RFID tag with a sensing function is a RFID sensor. In certain embodiments, a RFID tag with a sensing region is a RFID sensor.

In certain embodiments, a resonant sensor may comprise a RFID tag with an added sensing function as, for example, when an antenna of the RFID tag also performs sensing functions by changing its complex impedance parameters as a function of environmental changes. The determinations of environmental changes with such resonant sensors are performed by analysis of complex impedance. In one embodiment, a RFID tag may be converted into a RFID resonant sensor by coupling a complementary sensor across antenna and or/memory chip of the RFID tag. By coupling the complementary sensor, electrical response of the attached sensor may be translated into corresponding change in one or more of a complex impedance response of the resonant sensor. Non-limiting examples of the complex impedance response of the resonant sensor may include a resonance peak position, a peak width, a peak height and peak symmetry of the complex impedance response of the resonant sensor, magnitude of the real part of the complex impedance, resonant frequency of the imaginary part of the complex impedance, anti-resonant frequency of the imaginary part of the complex impedance, zero-reactance frequency, phase angle, and magnitude of impedance.

In certain embodiments, the resonant sensors may be used to measure a variety of physical, chemical and biological parameters. In RFID resonant sensors, the methods and systems for integrated interrogation may be used to collect both digital and analog signals from the RFID sensor to obtain digital or analog data (e.g. tag ID, end-user stored information, sensing information, any other digital information available from the tag) corresponding to the RFID tag, and analog data (e.g., sensing measurements, reflected power measurements) corresponding to the RFID sensors. In one embodiment, the RFID tag of the RFID sensor may be a passive tag. A passive RFID tag does not need a battery for its function and comprises a memory chip that is connected to the sensor antenna.

In some embodiments, the resonant sensor impedance spectra may be processed to extract several "spectral parameters". The spectral parameters are $F_p$, $Z_p$, $F_1$, or $F_2$ and others. The sensor impedance spectrum may be transmitted to the central computing center for processing. In one example, the central computing center may analyze at least a portion of the impedance spectrum or spectral features using steady state or dynamic responses from the impedance reader. The steady state sensor response is a response from the sensor over a determined period of time, where the response does not appreciably change over the measurement time. Thus, measurements of steady state sensor response over time produce similar values. The dynamic sensor response is a response from the sensor upon a sudden change in the measured environmental parameter (temperature, pressure, chemical concentration, biological concentration, etc.) Thus, the sensor response does significantly change over the measurement time. Thus, measurements of dynamic sensor response over time produce dynamic signature of response. Non-limiting examples of the dynamic signature of the response include average response slope, average response magnitude, largest positive slope of signal response, largest negative slope of signal response, average change in signal response, maximum positive change in signal response, and maximum negative change in signal response.

In certain embodiments, several different approaches may be used for providing a single sensing region on a substrate of the sensor. In one embodiment, a sensing material or sensing film may be disposed on the sensing region to define the sensing region. The sensing material may be configured to alter the impedance response of the sensor. In another embodiment, a protecting material or protecting film may be disposed on the sensing region to define the sensing region. In this embodiment, the protecting material may be configured to separate electrodes of the sensing region from the sample. In yet another embodiment, a sensing region may be in direct contact with the sample. In this embodiment, the sensing region may be configured to have electrodes of the sensing region in direct contact with the sample.

As used herein, the terms "sensing material" or "sensing film" may include, but are not limited to, materials deposited onto the sensing region of the resonant sensor to perform the function of predictably and reproducibly affecting the complex impedance sensor response upon interaction with the environment. For example, a conducting polymer such as polyaniline changes its conductivity upon exposure to solutions of different pH. When such a polyaniline film is deposited onto the sensor, the complex impedance sensor response changes as a function of pH. Thus, such an RFID sensor works as a pH sensor. When such a polyaniline film is deposited onto the RFID sensor for detection in gas phase, the complex impedance sensor response also changes upon exposure to basic (for example, NH3) or acidic (for example HCl) gases. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, and any other sensor material. In order to prevent the material in the sensor film from leaking into the liquid environment, the sensor materials are attached to the sensor surface using standard techniques, such as covalent bonding, electrostatic bonding and other standard techniques known to those of ordinary skill in the art.

As used herein, the term "environmental parameters" or "environmental properties" refers to measurable environmental variables within or surrounding a multivariable sensor. In certain embodiments, the measurable environmental variables may include one or more of physical, chemical or biological properties. Non-limiting examples of the environmental parameters may include temperature, pH, oxygen content, pressure, material concentration, conductivity, dielectric property, and number of dielectric, metallic, chemical, or biological particles in the proximity or in contact with the sensor, dose of ionizing radiation, light intensity, or combinations thereof.

As used herein, the term "analyte" refers to a substance that includes any desirable measured environmental parameter. As used herein, the term "interference" includes any undesirable environmental parameter that undesirably affects the accuracy and precision of measurements with the sensor. As used herein, the term "interferent" refers to a fluid or an environmental parameter (e.g., temperature, pressure, light, etc.) that may produce an interference response by the sensor. As used herein, the term "resonance impedance" or "impedance" refers to measured sensor frequency response around the resonance of the sensor from which the sensor "spectral parameters" are extracted.

In certain embodiments, sensing electrodes that are disposed on the sensing region, are not affected by the measured sample. In certain embodiments, sensing electrodes that are disposed on the sensing region, are predictably affected by the measured sample and predictably change sensor response. In one embodiment, electrodes are made at least in part from the sensing material that is responsive to environment. In this embodiment, the electrodes are sensitive to the environment and may sense one or more of a chemical, biological or physical parameters. In one embodiment, electrodes are fabricated from an environmentally sensitive material. Depending on the application of the sensor, electrodes material is different. For example, for corrosion monitoring, nonlimiting examples of electrodes material are aluminum, copper, and steel. For chemical and biological monitoring, non-limiting examples of electrodes material are polyaniline, composite core-shell nanoparticles, ligand-coated nanoparticles, bare nanoparticles, nanowires, nanotubes, and nano sheets.

By applying a sensing material onto the sensing region of the resonant sensor and measuring the complex impedance of the resonant sensor, impedance response may be correlated to the biological or chemical or physical parameters. In certain embodiments, the sensitive material may undergo a detectable change upon exposure to trace concentrations of an analyte. In these embodiments, the trace concentrations may be measured by disposing the sensing material between the electrodes that constitute the resonant circuit. Thus, dielectric, dimensional, charge transfer, and other changes in the properties of the sensing material may be detected by the changes in the resonant properties of the circuit.

Advantageously, a resonant sensor having a single sensing region is configured to provide individual responses for each tested target or the target and interferences. For example, the resonant sensor having the sensing region may provide different responses corresponding to each of the analyte. By applying a multivariate analysis (e.g., a principal components analysis), the dimensionality of the complex impedance responses for each of analytes is reduced to a single data point. This processed data is further used for quantitation of targets and their mixtures. As used herein, 'multivariate analysis' refers to an analysis of signals where one sensor produces multiple response signals that are not substantially correlated with each other. The multiple response signals from the sensor may be analyzed using multivariate analysis tools to construct response patterns of exposures to different environmental conditions, such as, pressure or temperature or fluid composition. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

In one example, the resonant sensor having the sensing region may provide responses corresponding to various depths or biological features of the measured sample or physiological features of cells. The various responses may be analyzed using multivariate analysis. For example, the resonant sensor may be used to probe the sample at a plurality of frequencies; the responses corresponding to this plurality of frequencies may be analyzed using multivariate analysis to obtain information associated with different depths within the sample. In one embodiment, the plurality of frequencies may be produced simultaneously from a single sensing region.

In certain embodiments, the resonant sensor may be used to probe the sample at the same frequency with the responses corresponding to the plurality of electrode pairs from a single sensing region.

In certain embodiments, the complex impedance response of the sensor may be a multivariable response as more than one frequency may be utilized to measure sensor response across the resonance of the sensor. In certain embodiments, the complex impedance response of the sensor may be a multivariable response because more than one frequency may be utilized to measure sensor response outside the resonance of the sensor. In some embodiments, the sensor response is measured at multiple frequencies across the resonance of the sensor. For example, if the sensor resonates at about 13 MHz, the measured frequencies and associated sensor responses are measured from about 5 MHz to about 20 MHz. This multivariable response is analyzed by multivariate analysis. The multivariable response of the sensor includes the sensor's full complex impedance spectra and/or several individually measured properties, such as but not limited to, $F_p$, $Z_p$, $F_z$, $F_1$, $F_2$, $Z_1$, and $Z_2$. These and other measured properties are "spectral parameters". These properties include the frequency of the maximum of the real part of the complex impedance ($F_p$, resonance peak position), magnitude of the real part of the complex impedance ($Z_p$, peak height), zero-reactance frequency ($F_z$, frequency at which the imaginary portion of impedance is zero), resonant frequency of the imaginary part of the complex impedance ($F_1$), and anti-resonant frequency of the imaginary part of the complex impedance ($F_2$), signal magnitude ($Z_1$) at the resonant frequency of the imaginary part of the complex impedance ($F_1$), and signal magnitude ($Z_2$) at the anti-resonant frequency of the imaginary part of the complex impedance ($F_2$). Other parameters may be measured using the entire complex impedance spectra, for example, quality factor of resonance, phase angle, and magnitude of impedance. Multivariable response spectral parameters are described in U.S. Pat. No. 7,911,345 entitled "Methods and systems for calibration of RFID sensors", which is incorporated herein by reference.

In certain embodiments, the sensor may comprise a protective material. In certain embodiments, the protective material may include, but is not limited to, materials that protect the sensor from an unintended mechanical, physical or chemical effect while still allowing the measurements of the fluid in proximity to or in contact with the sensor to be performed. The fluid can be a gas, a liquid, or a solid, or a suspension of particles including biological particles, or tissue samples. For example, an estimated measurement may include fluid conductivity measurement wherein a protecting film separates the sensor from the fluid yet allows an electromagnetic field to penetrate into fluid. In one example, the protective material may include, but is not limited to, materials that protect the sensor from an unintended mechanical, physical or chemical effect in the presence of an interferent. In one example, the protective material may be a paper film that is applied on top of the sensor to protect the sensor from mechanical damage and abrasion. In another example, the protective material may be a polymer film that is applied on top of the sensor to protect the sensor from corrosion when placed in a liquid for measurements. In yet another example, the protective material may be a polymer film that is applied on top of the sensor for protection from shortening of the sensor's circuit when placed in a conducting liquid for measurements. In yet another example, the protective material may be a polymer film that is applied on top of the sensor for protection from fouling of the electrodes when placed in a conducting liquid for measurements. Non-limiting examples of such protective material used as films may comprise paper and polymeric films such as polyesters, polypropylene, polyethylene, polyethers, polycarbonate, polyethylene terephthalate, or combinations thereof. In one example, the film may be grown with an inorganic species via atomic layer deposition or chemical vapor deposition.

In certain embodiments, the protective material may facilitate direct measurements of the fluids in proximity to or in contact with the sensor to be performed. In these embodiments, the sensor may or may not include a protective material on the sensing region. Measurements of the fluids may be performed by determining the complex permittivity of the fluids. The resonant sensor responds to the change in the complex permittivity of the environment. The real part of the complex permittivity of the fluid is referred to as a "dielectric constant". The imaginary part of the complex permittivity of the fluid is referred to as a "dielectric loss factor". The imaginary part of the complex permittivity of the fluid is directly proportional to a conductivity of a fluid. Measurements with a single sensor may be performed for mixtures of fluids or individual fluids. These measurements may be used to determine compositions of the fluids. In one embodiment, mixtures of the fluids may be homogeneous or heterogeneous. Non-limiting examples of the homogeneous mixtures are salt in water, ethanol in water, sugar in water, water in milk. Non-limiting examples of heterogeneous mixtures are silicone in water, oil in water, benzene in water, cells in media, virus particles in blood, blood in tissue.

FIG. 1 illustrates a portion of a resonant sensor system employing a sensor assembly 10 configured to probe a fluid sample using a plurality of frequencies. The resonant sensor assembly 10 comprises a resonant sensor 12. The resonant sensor 12 is configured to detect chemical, physical or biological parameters of a sample. The sensor comprises a single sensing region 14. The sensing region 14 may be disposed on a substrate. In some embodiments, the substrate of the sensor 12 may be a dielectric substrate. The substrate may be a well plate. In this embodiment, the electrodes may be deposited on the well plate. It should be noted, a well of a well plate is a non-limiting example of an open sample container or an open flow-channel.

In certain embodiments, the sensor assembly 10 may further include a plurality of tuning elements 16. The plurality of tuning elements may be operatively coupled to the single sensing region 14 to define a plurality of resonant circuits. The tuning elements 16 along with the single sensing region 14 may define a plurality of resonant circuits. Each resonant circuit of the plurality of resonant circuits may include one or more tuning elements of the plurality of tuning elements.

In the illustrated embodiment, the plurality of tuning elements 16 is external to the sensor 12. However, in one embodiment, the tuning elements 16 may be disposed on the substrate of the sensor 12. In another embodiment, some of the plurality of tuning elements 16 may be external to the sensor substrate, while other tuning elements 16 may be disposed on the substrate. The tuning elements 16 may comprise a resistor, a capacitor, an inductor, a resonator, impedance transformer, or combinations thereof.

Each resonant circuit may be configured to resonate at a particular frequency. At least one resonant circuit may be configured to resonate at a frequency that is different from the resonating frequency of the other resonant circuits. By way of example, if the sensing region 14 includes a pair of electrodes, the tuning elements 16 may be a conductor, a capacitor, and an inductor to form an inductor-capacitor-conductor (LCR) resonant circuit. The tuning elements 16 may be electrically coupled to the sensing region 14. In one embodiment, the tuning elements 16 may be in parallel connection to the sensing region 14.

In certain embodiments, the different resonant circuits of the plurality of resonant circuits may be configured to resonate at different frequencies. The different resonant circuits may be configured to probe the fluid sample with a plurality of frequencies. The different frequencies may be used to probe a fluid sample at different depths.

In certain embodiments, the resonant sensor assembly 10 may comprise at least one electrode pair. In some embodiment, the at least one electrode pair may form a two-electrode structure, or a two inter-digital electrode structure. In certain other embodiments, the resonant sensor assembly may comprise at least two electrode pairs. In one embodiment, the two electrode pairs may form a four-electrode structure, or a four inter-digital electrode structure. In some embodiments, the resonant sensor assembly 10 may include multiple pairs of electrodes. In one embodiment, the multiple pairs of electrodes may form multiple electrode structure. In one embodiment, at least one electrode of the multiple electrode structure may include a size different from a size of other electrodes of the multiple electrode structure. In one embodiment, the plurality of pairs of electrodes forming multiple electrode structure may be used in tomography applications.

In one embodiment, at least one pair of the plurality of electrode pairs comprises an electrode gap which is different from the electrode gap of other pairs. In some embodiments, at least one pair of the plurality of electrode pairs is disposed at a determined distance from a bulk of the substrate. In one example, a dielectric material may be disposed between the substrate and at least one pair of electrodes of the plurality of electrode pairs. The dielectric material may be in the shape of support structures as discussed in detail with regard to FIG. 5.

In certain embodiments, the tuning elements may be configured to provide a common resonant frequency for two or more pairs of electrodes of the plurality of electrode pairs. The tuning elements may be configured to provide different resonant frequencies for two or more pairs of electrodes of the plurality of electrode pairs.

In certain embodiments, at least one of the plurality of electrodes may be configured to act as a global electrode and other electrodes of the plurality of electrode pairs may be configured to act as local electrodes.

In certain embodiments, at least one of the pairs of the plurality of electrode pairs may be disposed in a fluid, buffer solution, biologically relevant fluid, cell growth media, bodily fluid, or combinations thereof. In some of these embodiments, at least one of an electrode of the plurality of electrode pairs may include a protective material.

In the illustrated embodiment, the sensor assembly 10 may also include a multiplexer 18. The multiplexer 18 may be configured to facilitate electronic switching between the plurality of tuning elements 16. The multiplexer 18 may be configured to select one or more signals associated with the probing frequencies and forward the selected signal to an output device or a reader. In one embodiment, the multiplexer 18 may be configured to selectively send signals to an output device or a reader. The multiplexer 18 may be configured to send a plurality of signals simultaneously to a sensor reader. The multiplexer 18 may also be configured to select one or more portions of the sensing regions associated with the probing frequency and forward the selected signal to the reader.

In certain embodiments, the sensor 12 may be a RFID sensor. The RFID sensor may be made from a RFID tag. The RFID tag may use electronic tags for storing data. The RFID tag may include at least two components, namely an integrated circuit (memory chip) and an antenna. In one embodiment, the memory chip may be in galvanic connection to the resonant sensor assembly 10. The memory chip may be configured to store and process information, and modulate and demodulate a radio frequency signal. In one embodiment, the memory chip may also be used for other specialized functions, for example, the memory chip may include a capacitor. The memory chip can also contain an input for an analog signal. The antenna may be configured to receive and transmit the radio frequency signal. In certain embodiments, an integrated circuit memory chip may be galvanically coupled to the resonant sensor assembly.

Figure 2:
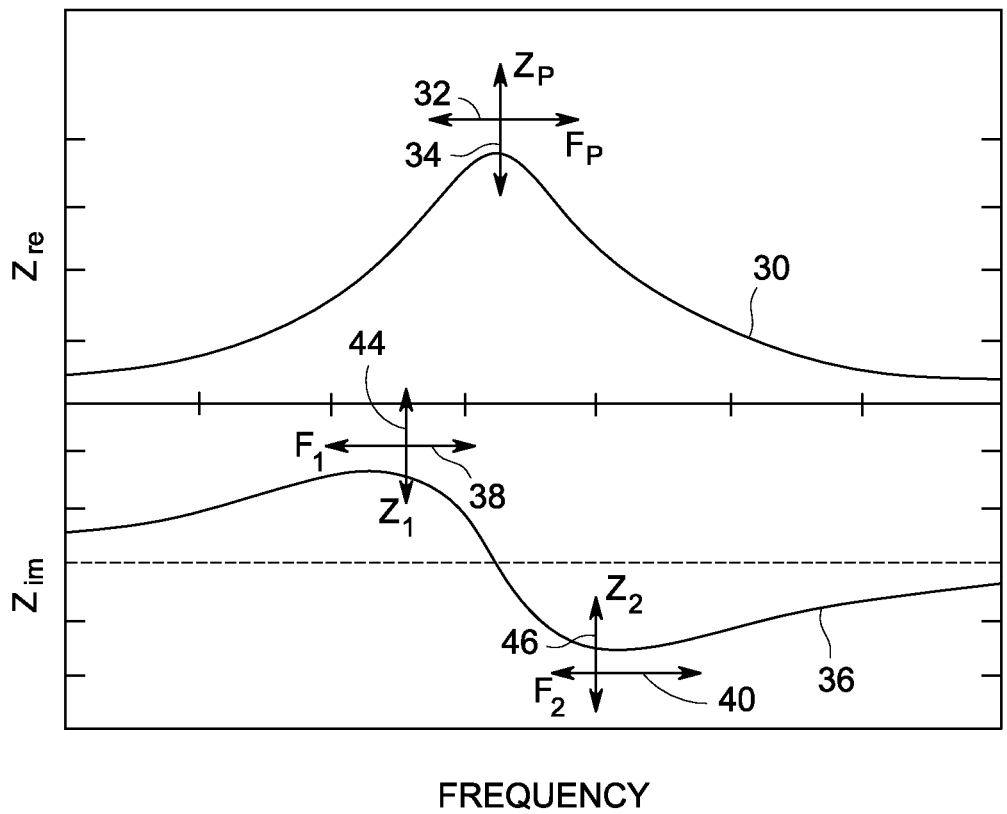
FIG. 2 is a graph of measured impedance parameters of an embodiment of the resonant sensor, in accordance with embodiments of the present technique.

FIG. 2 illustrates examples of real and imaginary portions of the impedance response spectrum of the sensor from a single resonant circuit. A plurality of such impedance response spectra may be generated by the plurality of resonant circuits of the single sensing region of a sensor. The origin of the impedance response spectra is either from the resonant circuit or the sensing region or both from the resonant circuit and the sensing region. As illustrated by the curve 30, the real part of the impedance includes spectral parameters $F_p$ 32 and $Z_p$ 34. The parameter $F_p$ 32 represents the frequency of the maximum of the real part of the impedance, and the parameter $Z_p$ 34 represents the magnitude of the real part of the impedance. Similarly, as illustrated by the curve 36, the imaginary part of the impedance includes $F_1$ 38, $F_2$ 40, $F_z$ 42, $Z_1$ 44, and $Z_2$ 46. The parameter $F_1$ 38 represents resonant frequency of the imaginary part of the impedance, and the parameter $F_2$ 40 represents anti-resonant frequency of the imaginary part of the impedance. The parameters $F_1$ and $F_2$ are related to different components of the equivalent circuit. The parameter $Z_1$ 44 represents signal magnitude at the resonant frequency of the imaginary part of the complex impedance $F_1$ 38. The parameter $Z_2$ 46 represents signal magnitude at the anti-resonant frequency of the imaginary part of the complex impedance $F_2$ 40. The parameter $F_z$ 27 represents the zero-reactance frequency. Additional non-limiting examples of the sensor parameters include parameters that can be extracted from the response of the equivalent circuit of the RFID sensor, the quality factor of resonance, phase angle, and magnitude of impedance of the resonance circuit response of the RFID sensor, and others known in the art. The difference between $F_1$ 38 and $F_2$ 40 may be related to real spectrum peak width. In this example, since $F_1$ 38 and $F_2$ 40 are related to different components of an equivalent circuit, $F_1$ 38 and $F_2$ 40 are not correlated. Peak symmetry may be affected by changes in impedance. Other parameters can be measured using the entire impedance spectrum, for example, using the quality factor of resonance, phase angle, and magnitude of impedance.

In one embodiment, the impedance analyzer may be configured to measure a complex resonant impedance (represented by Eq. (1)) of the sensor.

$$\check{Z}(f)=Z_{re}(f)+jZ_{im}(f) \quad \text{Eq. (1)}$$

It should be noted that $F_1$ and $Z_1$ originate from inductive resonance while $F_2$ and $Z_2$ originate from capacitive resonance.

In one example, the reader may measure the complex impedance of the sensor via a galvanic contact between the sensor and the reader. In another example, the reader may measure the complex resonant impedance of the sensor via inductive coupling between the sensor and the reader. The reader may be integrated into a mobile, handheld, or a stationary component.

Figure 3:
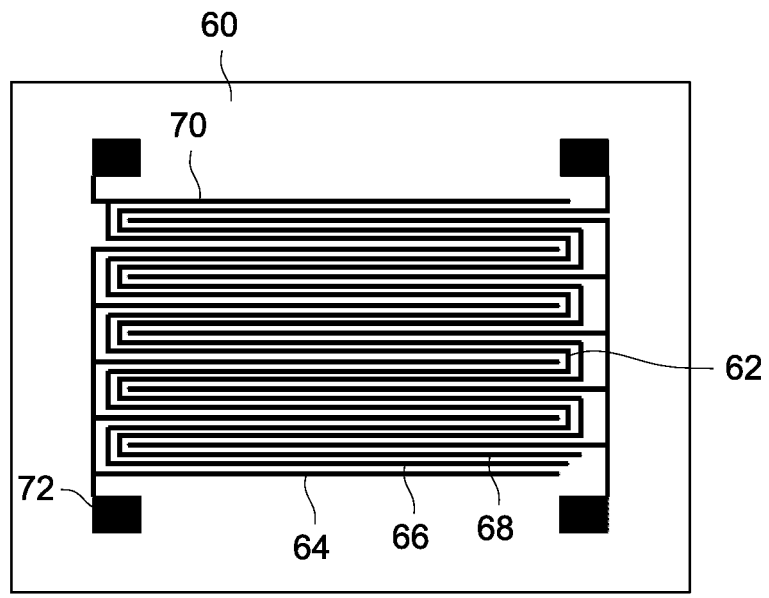
FIG. 3 is a schematic view of an example sensing region comprising a plurality of electrodes, in accordance with embodiments of the present technique.

FIG. 3 illustrates an example of a sensing region comprising a plurality of electrodes. In the illustrated embodiment, the portion of a sensor assembly includes a substrate 60 having a sensing region 62. The sensing region 62 may be disposed on a portion of the substrate 60. The substrate may be a dielectric substrate. The sensing region 62 includes four inter-digital electrodes 64, 66, 68 and 70.

The electrodes 64, 66, 68 and 70 in combination with tuning elements (not shown) may form a plurality of resonant circuits. One or more electrodes 64, 66, 68 and 70 may be a part of the resonant circuits. The electrodes 64, 66, 68 and 70 may be part of the same or different resonant circuits. The electrodes 64, 66, 68 and 70 may form pairs of electrodes when a reader in operative communication with the sensor is used to read the sensor response. Non-limiting examples of pairs of electrodes include a pair of electrodes 64 and 66, a pair of electrodes 64 and 68, a pair of electrodes 64 and 70, a pair of electrodes 66 and 68, a pair of electrodes 66 and 70, and a pair of electrodes 68 and 70.

At least one of the resonant circuit of the plurality of resonant circuits may be configured to resonate at a frequency that is different from resonating frequencies of other resonant circuits. The antenna or coil may be a part of the one or more resonant circuits. In certain embodiments, the resonating frequencies of a resonant circuit is decided by the tuning elements present in that particular resonant circuit. In certain embodiments, the four electrodes 64, 66, 68 and 70 may be electrically coupled to form two pairs of electrodes. In operation, the readout of the sensing region 62 may be performed using the electrodes 64, 66, 68 and 70. In certain embodiments, different resonant circuits may be used for providing different frequencies. The different frequencies may be used to detect fluid sample. The substrate 60 may further comprise contact pads 72 for the electrodes 64, 66, 68 and 70.

In one embodiment, at least a portion of the sensing region 62 may include a sensing material or sensing film. In another embodiment, at least a portion of the sensing region 62 may include a protective material. In one embodiment, the sensing region 62 may include a combination of the sensing material and protective material. In one such embodiment, the portions having the sensing material and protective material may be mutually exclusive. In a system with a plurality of electrodes, a plurality of combinations of sensing films and protective films in a sensing region may increase the dimensionality of the response, enabling simultaneous quantification of multiple parameters. In one example, the protective material may be disposed on the sensing material. In another example, a sensing material for detection of organic molecules of solvents in drinking, industrial, or environmental water may be deposited onto electrodes of the sensing region 62. In one embodiment, the sensing material may be in the form of a sensing film, the sensing film may be coated with a protective film to enhance the stability of the sensing film, Non-limiting examples of the sensing materials for a sensing film may include siloxane, polyurethane, silicone block polyimide polymer, monolayer-capped metal nanoparticles, or combinations thereof. Non-limiting example of a protective film material is a random copolymer of tetrafluoro ethylene and 2,2-bis(trifluoromethyl)-4,5-difluoro-1,3-dioxole (Teflon AF), or combinations thereof.

In some embodiments, the electrodes of the plurality of electrode pairs may comprise a protective material. In some of these embodiments, the protective material is deposited on some electrodes and not deposited on other electrodes. In one embodiment, the protective material may include a biologically compatible material.

The resonating frequency associated with a resonant circuit may depend on parameters, such as but not limited to, inductance value, capacitive value, resistance values of the resonant circuit, distance between the electrodes, or combinations thereof.

In embodiments where the plurality of electrode pairs include inter-digital electrodes, at least one pair of the plurality of electrode pairs may include an electrode gap which is different from the electrode gap of other pairs.

In some embodiments, at least one pair of the plurality of electrode pairs is configured to be electrically excited by a time varying electromagnetic signal. In some other embodiments, at least one pair of electrodes is disposed at a determined distance from a bulk/volume of the substrate. In these embodiments, a dielectric material may be disposed between the substrate and at least one pair of electrodes. In certain embodiments, at least one of the pair of the plurality of electrode pairs may be disposed in a biologically relevant fluid.

In certain embodiments, the tuning elements may be configured to provide a common resonant frequency for two or more pairs of electrodes of the plurality of electrode pairs.

Figure 4:
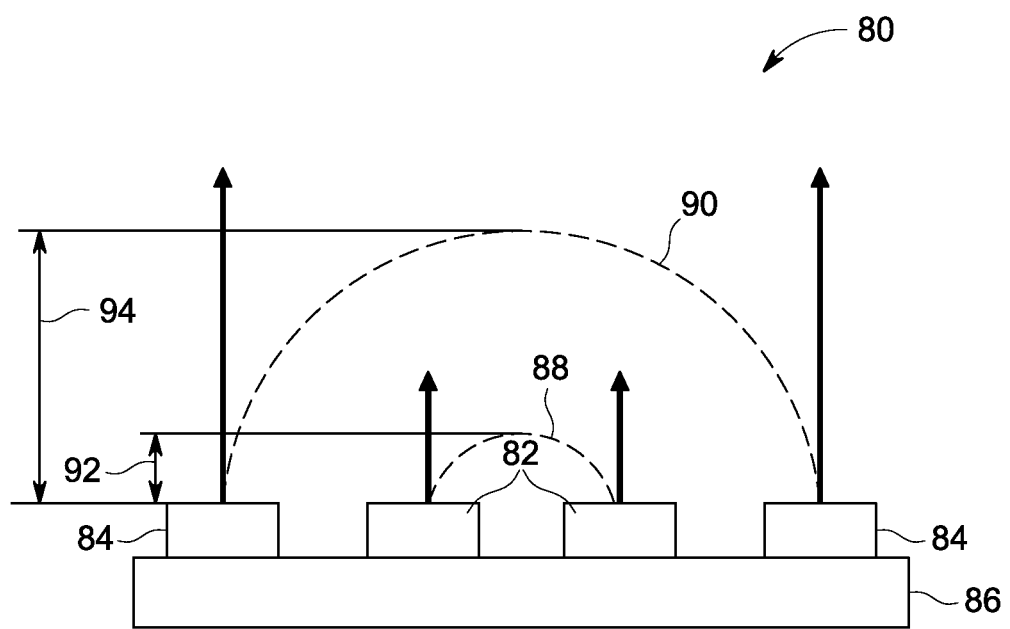
FIGS. 4-6 are schematic views of example sensing regions having a plurality of electrodes, in accordance with embodiments of the present technique.

FIG. 4 illustrates an example sensing region 80 having two pairs of electrodes, namely a first pair 82 and a second pair 84. The pairs 82 and 84 of the electrodes are disposed on a substrate 86. In one embodiment, the substrate may be a dielectric substrate. The substrate 86 may be a well plate, or a microfluidic substrate, or both.

In one embodiment, substrate 86 is made from a material that is configured to change its dielectric constant upon a controlled application of an external stimulus. The change of the dielectric constant of the substrate 86 may result in the change of the amount of electric field generated by the electrodes available to probe the sample fluid. Non-limiting examples of materials that undergo a change in the dielectric constant upon an application of an external stimulus include ferroelectric materials, para-electric materials, and liquid crystal materials. Non-limiting examples of external stimulus for the change of the dielectric constant of materials include applied voltage and applied optical radiation over ultraviolet-visible spectral range.

The first pair 82 of electrodes may form a first resonant circuit. The second pair 84 of electrodes may form a second resonant circuit. The first resonant circuit may have a readout generally represented by the reference numeral 88. Similarly, the second resonant circuit may have a readout generally represented by the reference numeral 90. The electric field readout is about perpendicular to the plane of the substrate.

In one embodiment, the resonant circuit comprising the first pair 82 of electrodes and the resonant circuit comprising the second pair 84 of electrodes are configured to resonate at different frequencies.

In another embodiment, the resonant circuit comprising the first pair 82 of electrodes and the resonant circuit comprising the second pair 84 of electrodes are configured to resonate at same frequency.

In the illustrated embodiment, the resonant frequency of the pair 82 of electrodes is different from the resonating frequency of the pair 84 of electrodes. The electric field 88 that exists between the pair 82 of electrodes has a different penetration depth 92 as compared to the electric field 90 that exists between the pair 84 of the electrodes. The electric fields 88 and 90 with different penetration depths facilitate analysis of fluid samples at different depths.

In the presence of contamination of the sensor, the pair of electrodes with less distance between the electrodes may be used to probe contamination or debris or fouling. The pair of electrodes with more distance between the electrodes may be used to detect the fluid sample. The debris and fouling effect may be thus subtracted to acquire actual values representative of fluid sample.

In certain embodiments, the electrodes may be coated with biologically compatible protective dielectric film that allows electrodes to operate in highly electrically conducting medium without getting electrically shortened. Pairs of electrodes 82 and 84 can be coated with different sensing materials, or a sensing material and a protective material or with protective materials of different thickness or different dielectric constant. These diverse types of coatings increase the dimensionality of the sensor response, enabling simultaneous quantification of multiple parameters.

It should be noted that during operation of a sensor assembly the electric field readout emanates from the electrodes and is present in a direction away from the substrate as well as in the direction towards the substrate. However, the dielectric material of the substrate partially absorbs the electric field readout that is directed towards the substrate. Hence, only half of the readout (readout directed away from the substrate) is used by the sensor is typically used to analyze the sensor response.

Advantageously, the elevation of the electrodes above the substrate increases the amount of the electric field that is available for the interaction with the sample.

Figure 5:
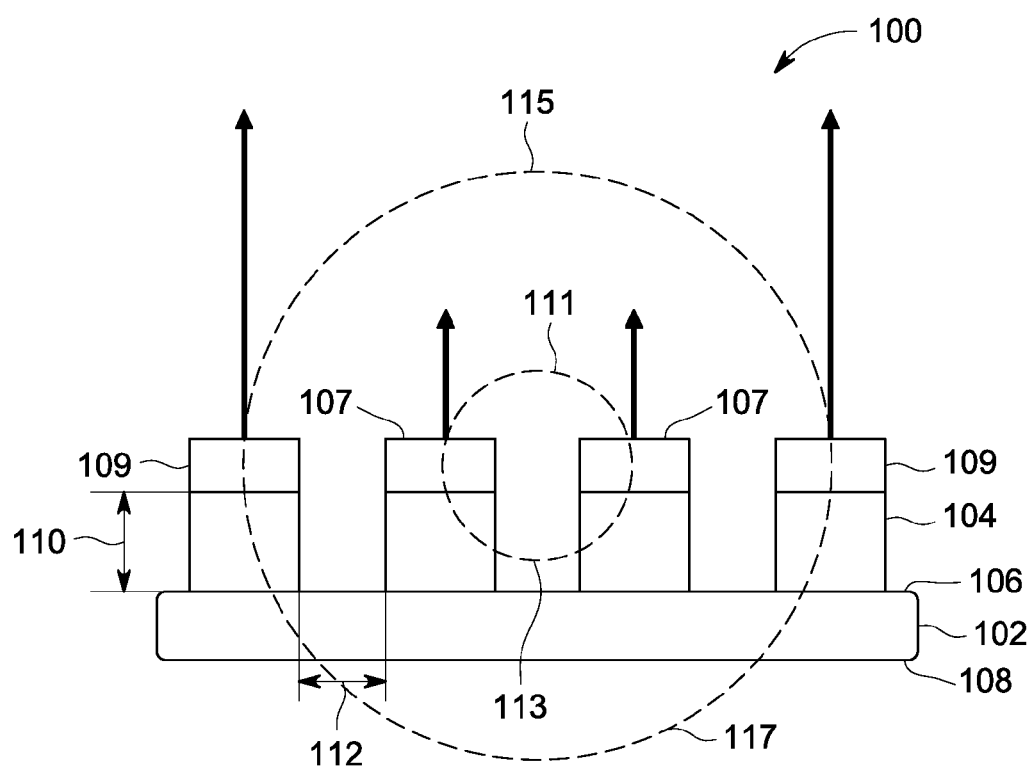

Turning now to FIG. 5, a portion of a sensing region 100 having a substrate 102. The substrate 102 may be a dielectric substrate having a first side 106 and a second side 108. The substrate 102 may include one or more support structures 104. The support structures 104 may be formed on a first side 106 of the substrate 102. Alternatively, the support structures 104 may be formed separately and coupled to the substrate 102 subsequently. Pairs 107 and 109 of the electrodes may be disposed on the support structures 104.

The first pair 107 of electrodes may form a first resonant circuit. The second pair 109 of electrodes may form a second resonant circuit. The first resonant circuit may have a readout generally represented by the reference numerals 111 and 113. The second pair 109 of electrodes may form a second resonant circuit. The second resonant circuit may have a readout generally represented by the reference numerals 115 and 117. In the illustrated embodiment, the support structures 104 may be configured to reduce the adverse effect of the substrate 102 on the electric fields 113 and 117.

In one embodiment, the support structures 104 may be formed of the same material as that of the substrate 102. In another embodiment, the support structures 104 may be made of a different material than that of the substrate 102. Suitable materials for support structures 104 may include materials that are less energy loss materials. The materials of the support structures 104 may be such that an imaginary part of a complex permittivity of the material of the support structures 104 may be about zero. Further, the real part of the complex permittivity of the material of the support structures 104 may be about. Non-limiting examples of such materials may include dielectric materials, such as but not limited to, aerogel, KAPTON, liquid crystal polymer (LCP), silica, or combinations thereof.

In certain embodiments, the height "h", generally represented by the reference numeral 110 may be same or different for the different electrodes of the sensing region. In one embodiment, the height 110 of the support structures 104 may depend on the distance 112 between the electrodes. The height of the support structures may be adjusted based on the depth of the electric field that is required to penetrate. In one embodiment, the height 110 of the support structures 104 may be decided based on the desirable distance between the electrodes and is in the range from 0.1 to 10 of the distance 112 between the electrodes.

Figure 6:
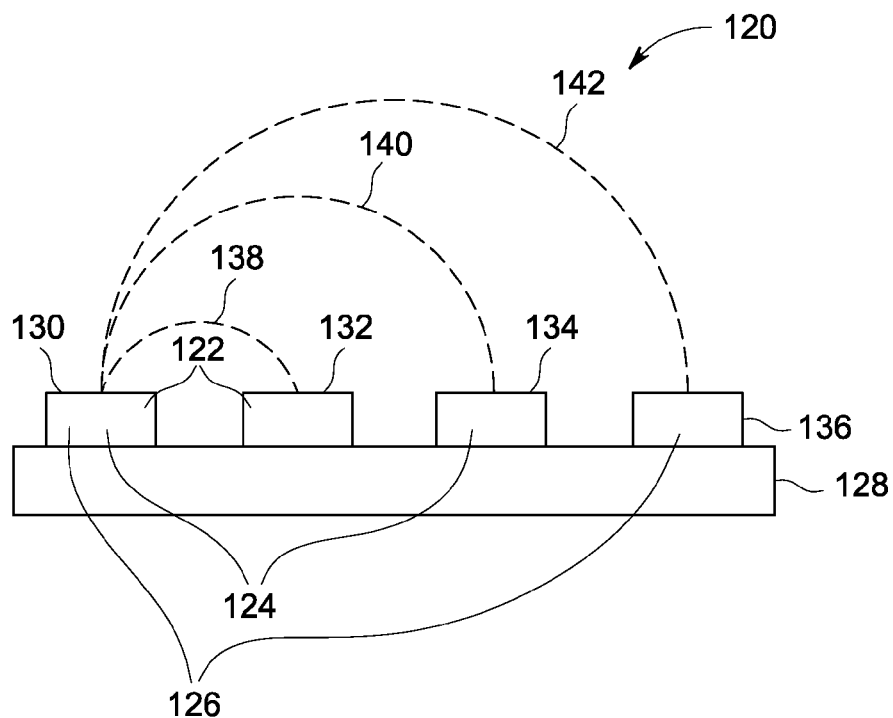

FIG. 6 illustrates a portion of a sensing region 120 having pairs of electrodes, namely a first pair 122 having electrodes 130 and 132, a second pair 124 having electrodes 130 and 134, and a third pair 126 having electrodes 130 and 136. The pairs 122, 124 and 126 of electrodes are disposed on a substrate 128. The electrode 130 is a global electrode, while electrodes 132, 134, 136 are local electrodes. In certain embodiments, the global electrodes are the electrodes that are used to induce signals between global and local electrodes. In one embodiment, the global electrodes may be common across all local electrodes. In some embodiments, the local electrodes are electrodes that are individually associated with a global electrode. External tuning and multiplexing components may be connected between the global electrode and the plurality of local electrodes to create multiple resonant circuits. The pairs 122, 124 and 126 form three different resonant circuits having readouts generally represented by reference numerals 138, 140 and 142, respectively. The external components allow for simultaneous or sequential frequency measurements and tuning of the resonator circuit pairs.

As discussed above, the sensor is configured to resonate at various frequencies. Hence, a single sensor is configured to probe a fluid sample at a plurality of frequencies. The sensing region may be activated electronically using a plurality of tuning elements, where the tuning elements along with the sensing region form resonant circuits.

Figure 7:
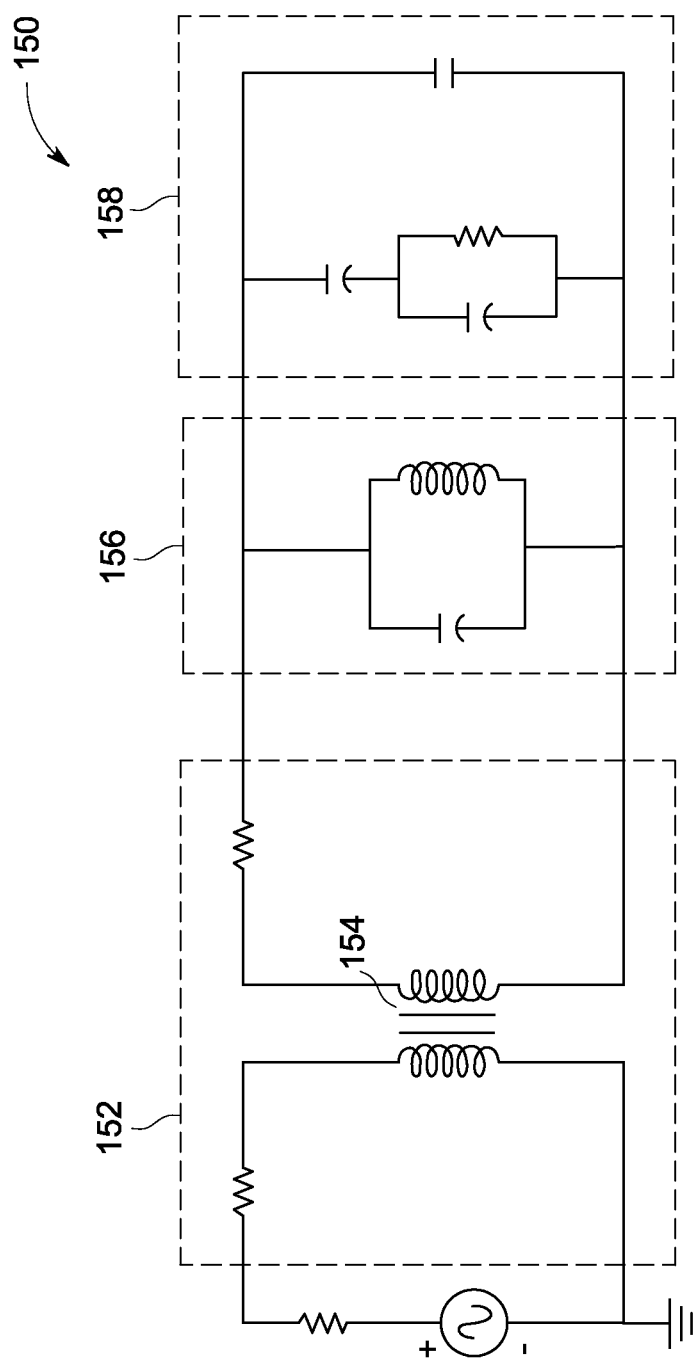
FIG. 7 is an equivalent circuit of electrode/sample structure with a re-configurable design, in accordance with embodiments of the present technique.

FIG. 7 illustrates an equivalent circuit of electrode/cell structure 150 with a re-configurable design. In the illustrated embodiment, the block 152 represents inductively coupled excitation. In the illustrated embodiment, a pick-up coil operatively coupled to network analyzer may be configured to drive electromagnetic signal wirelessly. Alternatively, the network analyzer itself may be configured to drive the electromagnetic signal. The electromagnetic signal may be transferred using a wired or a wireless connection. In one embodiment, the pick-up coil may be configured to transfer the electromagnetic signal to the receiving antenna for excitation of the sensor. The transformer 154 inside the block 152 represents this electromagnetic energy conversion and inductive coupling between the sensor and the pickup coil of the reader. The block 156 represents tuning circuit with R, L, C components. The tuning circuit 156 may change operating frequency range by varying the values of R, L, C, or combinations thereof. The block 158 represents an equivalent circuit of fluid sample comprising a plurality of combinations of Rs and Cs. In one embodiment, the tuning circuit 156 may include a plurality of switches to realize a plurality of combinations of the R, L, C components and a plurality of combinations of connections. Using the plurality of switches, in addition to the resonant frequency tuning it is possible to realize magnitude tuning to provide enhanced matching impedance to the sensing regions. In certain embodiments, a plurality of combinations of connections, e.g., series, parallel, and combination of series and parallel connections of R, L, C components may be realized.

Figure 8:
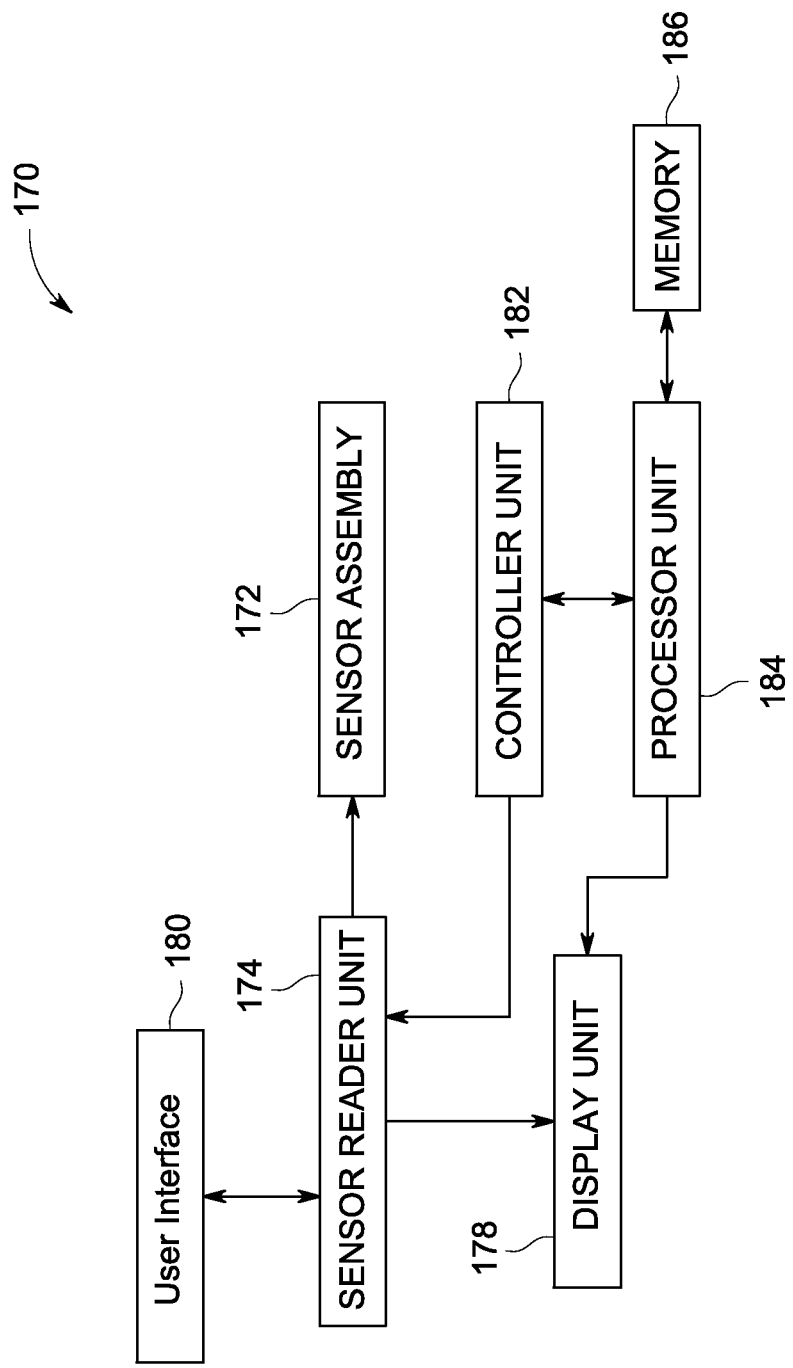
FIG. 8 is a schematic representation of a sensor system employing a single sensor region, in accordance with embodiments of the present technique.

FIG. 8 illustrates a resonant sensor system 170 comprising a sensor assembly 172, a sensor reader unit 174, and a display unit 178. The system 170 may further comprise a user interface 180, a controller unit 182 and a processor unit 184. The user interface 180, such as but not limited to a mouse, keyboard, touchscreen, or the like, may allow the operator or user to select options by touching displayed graphics, icons, and the like displayed on the touchscreen.

The sensor reader unit 174 may comprise a sensor reader. The sensor reader may be operatively coupled to the sensor assembly 172 using a wired or wireless combination. The display unit 178 may include one or more monitors that display analyzed information representing the cell, to the user for review and analysis. The display 178 may automatically display, for example, 2D or 3D data stored in a memory 186 or currently being acquired, this stored data may also be displayed with a graphical representation by the display unit 178.

In one example, the controller unit 182 may be used to control the electronic switching of the resonant circuits. In one embodiment, the electronic switching may be performed with a controller unit 182 incorporated into the sensor reader unit 174. The desirable switching configuration may be prefed, or may be provided using the input device 180.

The processor unit 184 may be configured to process the signals from the sensor assembly 172. In one embodiment, the processor unit 184 may be configured to perform one or more processing operations. By way of example, the processor unit 184 may be configured to process a plurality of signals from the plurality of resonant circuits. Acquired signals may be processed in real-time during analysis and detection of the fluid sample. Additionally or alternatively, the signal information may be stored temporarily in the memory 186. The memory 186 may comprise any known data storage medium, for example, temporary or permanent storage mediums or removable storage mediums.

Figure 9:
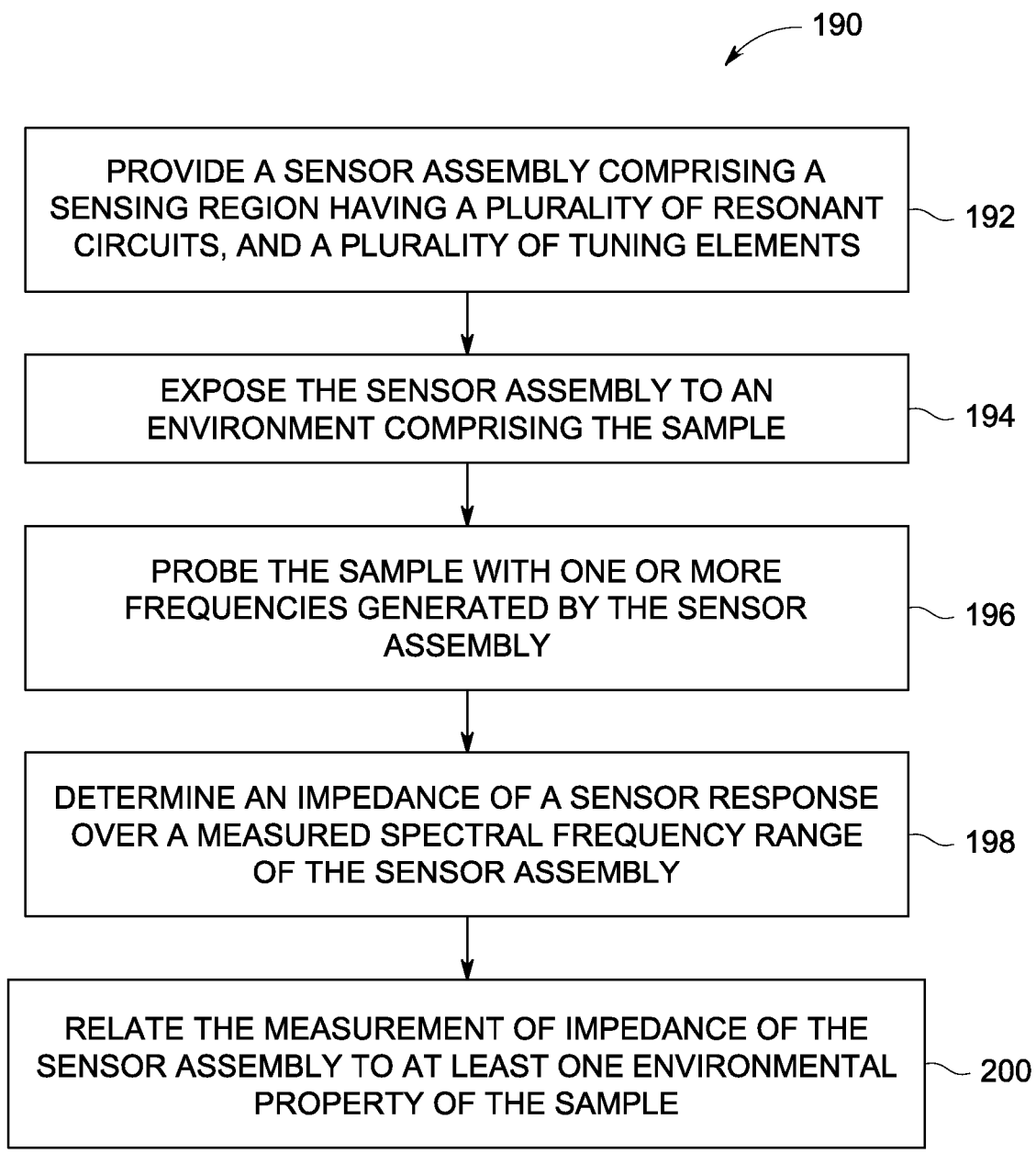
FIG. 9 is a flow chart for a method for analyzing a sample, in accordance with embodiments of the present technique.

FIG. 9 illustrates a flow chart 190 for a method for analyzing a sample. Non-limiting examples of the sample may include biological molecules, biological assemblages, organic molecules, organic material, biological material, inorganic material. In some embodiments, the sample may include biological molecules, biological assemblages, organic molecules, organic material, biological material, inorganic material, or combinations thereof. In one embodiment, the sample may include proteins, viral species, cells, bacteria, or combinations thereof. In certain embodiments, the sample may be a liquid sample, a gaseous sample, a solid sample, or combinations thereof.

At step 192, the method begins by providing a sensor assembly comprising a single sensing region having a plurality of resonant circuits, and a plurality of tuning elements. In one embodiment, providing the sensor assembly may include providing a well plate, and depositing a plurality of electrodes on the well plate. In one embodiment, a single sensing region may be deposited per well on the well plate. In another embodiment, at least two sensing regions may be provided per well on the well plate.

At step 194, the sensor assembly is exposed to an environment comprising the sample.

In certain embodiments, the method includes providing a sensor assembly having a plurality of electrode pairs. In some of these embodiments, the method may include electrically exciting at least one pair of electrodes of the plurality of electrode pairs by a power varying electromagnetic signal.

In one embodiment, the method may include electrically exciting at least one pair of electrodes of the plurality of electrode pairs by a time varying electromagnetic signal.

In one example, the time varying electromagnetic signal may be modulated by power, frequency, amplitude, or combinations thereof.

In certain embodiments, the sensor assembly may include a plurality of electrode pairs, wherein the method comprises electrically exciting at least one pair of electrodes of the plurality of electrode pairs by a power varying electromagnetic signal.

In one embodiment, the sensor assembly may include a plurality of electrode pairs, where at least one electrode of the plurality of electrode pairs may be configured to act as a global electrode and other electrodes of the plurality of electrode pairs may be configured to act as local electrodes. where the global electrode is configured to induce a response in the local electrodes. In one example, a four electrode structure may be driven by global electrodes, and driving a read out by local electrodes. Additionally, the method may include directly measuring the local electrodes by a reader. In one embodiment, the global electrode induces and returns a response in the local electrodes.

In another embodiment, the method may include individually driving the local eletrodes, and acquiring responses using the global electrode is configured to acquire the responses.

In some embodiments, the method may include electrode system, driven by global electrodes and read out driven by small resonant local electrodes. In some of these embodiments, large pickup coils may be used for driving a plurality of resonant sensors. In some embodiments, electrical contacts may be provided to each sensing region. In other embodiments, advanced multiplexing may be used to allow individual response from the plurality of sensors. It should be noted that a plurality of multiplexing methods are available and not limited by time-, code- and frequency-division multiplexing. In certain embodiments, time-division multiplexed sensors may be addressed in sequence, thereby allowing direct measurement of each sensing region at the expense of time. In some embodiments, frequency- and code-division multiplexed sensing regions may use broadband or digitally modulated sources to allow simultaneous detection at the expense of increased complexity of the analyzer.

At step 196, the sample is probed using one or more frequencies generated by the sensor assembly. In one embodiment, the one or more frequencies may be selected based on frequency dependent dielectric properties of a sample material in presence or absence of external stimuli. In one embodiment, the external stimuli may include an electrical field, a magnetic field, radiation, an acoustic field, a mechanical field, a thermal field, ionizing radiation, a pharmacologic stimulus, or combinations thereof.

In one embodiment, the measurements may be performed using a plurality of resonant circuits. In another embodiment, the measurements are performed without resonant circuits.

Additionally, the method includes adjusting one or more electrical parameters of the tuning elements to tune resonating frequencies corresponding to the one or more of the plurality of resonant circuits. Further, the method comprises switching between the plurality of resonant circuits.

In one embodiment, the method includes measuring a sensor signal using a plurality of resonant circuits. In another embodiment, the method includes measuring a sensor signal using a plurality of tuning elements and without resonant circuits.

In certain embodiments, the sensor signal may be measured over a frequency range of a circuit resonance. In some embodiments, the method includes measuring over a frequency range of a circuit resonance and outside a frequency range of the circuit resonance.

In embodiments where the sensor assembly comprises a plurality of electrode pairs, the plurality of electrode pairs may be addressed with a time-division multiplexing, a code division multiplexing, frequency division multiplexing, or combinations thereof.

In certain embodiments, time division multiplexing may include using one analyzer to serially probe each sensing assembly using a multiplexer. In some embodiments, frequency or code division multiplexing (FDM) may include using common receivers. In certain embodiments, the way each sensor is driven may be changed. In the case of frequency division multiplexing, each sensor may be driven at a unique frequency and the response of all the channels may be acquired by a common global electrode. The analyzer may be configured to map the responses to their respective sensors based on the response frequency. For RF, it may be desirable to have a narrow bandwidth signal for the excitation to allow a reasonable number of electrodes. In the case of code division multiplexing, the sensors may be driven at the same carrier frequency. The driving signal into each region may be divided with orthogonal codes. The analyzer may be configured to correlate the mixed signal with each code to separate each channel.

At step 198, a complex impedance of the sensor response may be determined over a measured spectral frequency range of the sensor assembly.

At step 200, the measurement of impedance of the sensor assembly may be related to one or more parameters.

In one embodiment, the method includes modeling a sensor response using principal components analysis. In another embodiment, the method includes modeling a sensor response using partial least squares. In yet another embodiment, the method includes modeling a sensor response using equivalent circuit models and multiple nonlinear regression. In one example, the equivalent circuit model may be automatically configured through genetic algorithms. In another example, the equivalent circuit model regression guess coefficients may be automatically estimated through genetic algorithm or multiple passes.

In one non-limiting example, measurements may be performed using a plurality of resonant circuits with sensing regions positioned in individual wells of a well plate. In one embodiment, each sensing region may include at least a four inter-digital electrode structure. In one example, the measurements may be performed within a frequency range of the sensor resonance. In another example, the measurements may be performed outside a frequency range of the sensor resonance In one embodiment, the measurements may be performed over the frequency range of the circuit resonance. In another embodiment, the measurements may be performed over the frequency range of the circuit resonance and outside the frequency range of the circuit resonance.

In one embodiment, the frequencies may be selected based on frequency dependent dielectric properties of a sample material in presence or absence of external stimuli.

Optionally, the one or more electrical parameters of the tuning elements may be adjusted to tune resonating frequencies corresponding to the one or more of the plurality of resonant circuits to desirable frequencies. In one example, the resonating frequencies of the resonating circuits may be tuned such that each of the plurality of resonating circuits have a resonating frequency which is different from the resonating frequency of the other resonating circuits.

In some embodiments, the method may further comprise electronic switching between the plurality of resonant circuits.

In certain embodiments, a method for analyzing a sample may include determining resonance impedance spectra of a sensor response over a measured spectral frequency range of the sensor assembly, applying multivariate statistical analysis to the resonance impedance spectra of a sensor response to obtain multivariate response factors, and relating the multivariate response factors to at least one environmental property of the sample.

In one embodiment, at least two resonances generated by the sensor assembly are fundamental resonances. In one example, the method may include obtaining the at least two resonances generated by the sensor assembly by applying different power levels of the sensor excitation. In one embodiment, at least two resonances generated by the sensor assembly may comprise a fundamental resonance and at least one harmonic resonance of the resonant circuit. In one example, the at least two resonances generated by the sensor assembly may include harmonic resonances of the resonant circuit.

Advantageously, the systems and methods facilitate probing the fluids at various frequencies using a single sensor having a single sensing region that is configured to resonate at a plurality of frequencies. Also, a resonant sensor having a single sensing region is configured to provide individual responses for each tested target or the target and interferences. Further, since the systems and methods facilitate probing a sample with a plurality of frequencies while using a single sensor, it is not required to dispose the fluid sample on a plurality of sensors to probe the cell with a plurality of frequencies.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A resonant sensor assembly, comprising:
a dielectric substrate comprising a sensing region, wherein the sensing region comprises a plurality of electrode pairs having corresponding electrode gaps, and wherein at least one electrode pair of the plurality of electrode pairs comprises an electrode gap which is different from electrode gaps of other electrode pairs of the plurality of electrode pairs; and
a plurality of tuning elements operatively coupled to the sensing region, wherein the sensing region is coupled to the plurality of tuning elements to define a plurality of resonant circuits, and wherein each electrode pair of the plurality of electrode pairs forms a resonant circuit in combination with one or more tuning elements of the plurality of tuning elements.

2. The resonant sensor assembly of claim 1, wherein at least one of the electrodes of the plurality of electrode pairs comprises an inter-digital electrode.

3. The resonant sensor assembly of claim 1, wherein at least one electrode pair of the plurality of electrode pairs is disposed at a determined distance from a bulk of the dielectric substrate.

4. The resonant sensor assembly of claim 1, comprising a dielectric material disposed between the dielectric substrate and at least one electrode pair of the plurality of electrode pairs.

5. The resonant sensor assembly of claim 1, wherein the plurality of tuning elements are configured to provide a common resonant frequency for two or more electrode pairs of the plurality of electrode pairs.

6. The resonant sensor assembly of claim 1, wherein the plurality of tuning elements is configured to provide different resonant frequencies for two or more electrode pairs of the plurality of electrode pairs.

7. The resonant sensor assembly of claim 1, wherein the plurality of electrode pairs comprises a two electrode structure.

8. The resonant sensor assembly of claim 7, wherein the two electrode structure comprises a two inter-digital electrode structure.

9. The resonant sensor assembly of claim 1, wherein the plurality of electrode pairs comprises a four inter-digital electrode structure.

10. The resonant sensor assembly of claim 1, wherein the plurality of electrode pairs comprises a multiple electrode structure.

11. The resonant sensor assembly of claim 10, wherein at least one electrode of the multiple electrode structure comprises a size different from a size of other electrodes of the multiple electrode structure.

12. The resonant sensor assembly of claim 1, wherein at least one electrode of the plurality of electrode pairs is configured to act as a global electrode and other electrodes of the plurality of electrode pairs are configured to act as local electrodes.

13. The resonant sensor assembly of claim 1, wherein at least one electrode pair of the plurality of electrode pairs is disposed in a fluid, buffer solution, biologically relevant fluid, cell growth media, bodily fluid, or combinations thereof.

14. The resonant sensor assembly of claim 1, wherein at least one electrode of the plurality of electrode pairs comprises a protective material.

15. The resonant sensor assembly of claim 1, wherein at least a portion of the sensing region comprises a protective layer.

16. The resonant sensor assembly of claim 15, wherein the protective layer comprises a biologically compatible layer.

17. The resonant sensor assembly of claim 1, wherein the dielectric substrate comprises a well plate.

18. The resonant sensor assembly of claim 1, further comprising an integrated circuit memory chip galvanically coupled to the resonant sensor assembly.

19. The resonant sensor assembly of claim 1, wherein one or more of the plurality of tuning elements comprise capacitors, resistors, inductors, impedance transformers, or combinations thereof.

20. A system, comprising:
a resonant sensor assembly, comprising:
  a dielectric substrate comprising a sensing region, wherein the sensing region comprises a plurality of electrode pairs having corresponding electrode gaps, and wherein at least one pair of the plurality of electrode pairs comprises an electrode gap which is different from electrode gaps of other electrode pairs of the plurality of electrode pairs;
  a plurality of tuning elements operatively coupled to the sensing region wherein the sensing region is coupled to the plurality of tuning elements to define a plurality of resonant circuits, wherein each electrode pair of the plurality of electrode pairs forms a resonant circuit in combination with one or more tuning elements of the plurality of tuning elements; and
a reader in operative communication with the resonant sensor assembly, wherein the reader is configured to acquire responses at a plurality of frequencies.

21. The system of claim 20, wherein the resonant sensor assembly is employed in a tomography system.

22. A resonant sensor assembly, comprising:
a dielectric substrate comprising a sensing region having at least four inter-digital electrode structure, wherein the four inter-digital electrode structure comprises one or more electrode pairs, and wherein at least one electrode pair of the four inter-digital electrode structure comprises an electrode gap which is different from electrode gaps of other electrode pairs of the four inter-digital electrode structure;
a plurality of tuning elements operatively coupled to the sensing region to define a plurality of resonant circuits, wherein one or more electrodes of the four inter-digital electrode structure form one or more resonant circuits in combination with one or more tuning elements of the plurality of tuning elements, and
wherein the plurality of tuning elements are configured to provide predetermined resonant frequencies associated with the one or more electrode pairs.

* * * * *